(12) United States Patent
Prior et al.

(10) Patent No.: US 10,674,961 B2
(45) Date of Patent: Jun. 9, 2020

(54) UNIVERSAL FINGERTIP SENSOR

(71) Applicant: Nonin Medical, Inc., Plymouth, MN (US)

(72) Inventors: Matthew Prior, Plymouth, MN (US); Gregory J. Rausch, Minnetonka, MN (US); Marcus A. Kramer, Circle Pines, MN (US)

(73) Assignee: Nonin Medical, Inc., Plymouth, MN (US)

( * ) Notice: Subject to any disclaimer, the term of this patent is extended or adjusted under 35 U.S.C. 154(b) by 86 days.

(21) Appl. No.: 15/592,897

(22) Filed: May 11, 2017

(65) Prior Publication Data

US 2017/0325742 A1    Nov. 16, 2017

Related U.S. Application Data

(60) Provisional application No. 62/334,708, filed on May 11, 2016.

(51) Int. Cl.
*A61B 5/1455* (2006.01)
*A61B 5/00* (2006.01)

(52) U.S. Cl.
CPC ........ *A61B 5/6826* (2013.01); *A61B 5/14552* (2013.01); *A61B 5/14553* (2013.01); *A61B 5/6838* (2013.01); *A61B 5/002* (2013.01); *A61B 2562/0238* (2013.01); *A61B 2562/04* (2013.01); *A61B 2562/227* (2013.01)

(58) Field of Classification Search
CPC ............... A61B 5/6826; A61B 5/6838; A61B 2562/0238; A61B 5/1455
See application file for complete search history.

(56) References Cited

U.S. PATENT DOCUMENTS

2010/0210924 A1* 8/2010 Parthasarathy ...... A61B 5/0002
600/301
2016/0374558 A1* 12/2016 Ishikawa ............. A61B 5/0059
600/473

* cited by examiner

*Primary Examiner* — Eric F Winakur
*Assistant Examiner* — David Joseph Fernandez-Fidalgo
(74) *Attorney, Agent, or Firm* — Schwegman Lundberg & Woessner, P.A.

(57) ABSTRACT

A device includes a digit probe, a plurality of optical elements, a processor, and a communication module. The digit probe has an interior surface and has an exterior surface. The interior surface is configured to engage a digit and the exterior surface is configured to engage a tissue site associated with the digit. The plurality of optical elements is coupled to at least one of the interior surface and the exterior surface. The plurality of optical elements includes at least one emitter and includes at least one detector. The processor is coupled to the plurality of optical elements. The processor is configured to generate a measure of arterial oxygenation corresponding to the digit and configured to generate a measure of regional oxygenation corresponding to the tissue site. The communication module is coupled to the processor. The communication module is configured to communicate the measure of arterial oxygenation and regional oxygenation with a remote device.

11 Claims, 5 Drawing Sheets

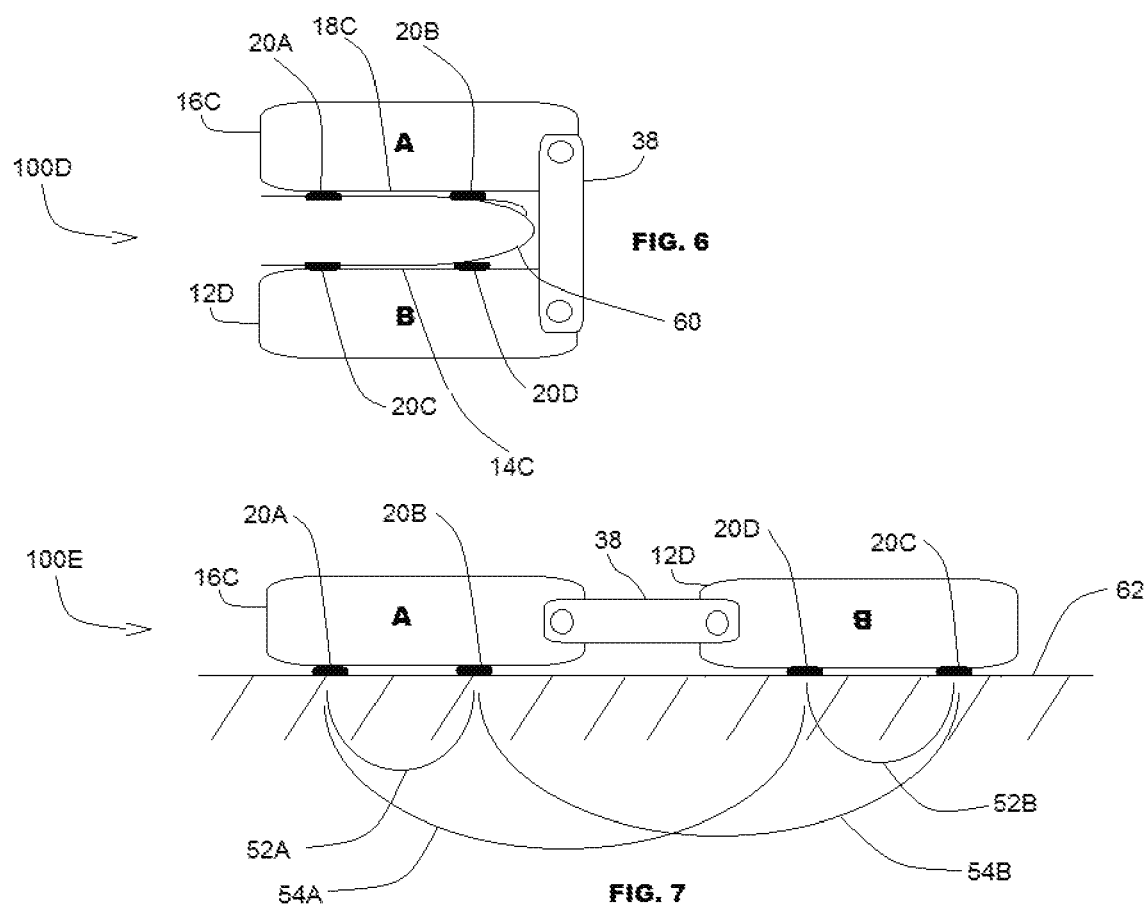

UNIVERSAL FINGERTIP SENSOR

CLAIM OF PRIORITY

This patent application claims the benefit of priority of U.S. Provisional Patent Application Ser. No. 62/334,708, filed on 11 May 2016, which is hereby incorporated by reference herein in its entirety.

BACKGROUND

Pulse oximetry provides a measure of the oxygenation in arterial blood. Regional oximetry, sometimes referred to as tissue oximetry can provide a measure of organ health associated with oxygenation of the organ tissue. These different measurements of oxygenation are determined using emitted light of different optical wavelengths and using different algorithms. For example, with pulse oximetry, arterial blood exhibits a pulsatile behavior which facilitates measurement of oxygen content. On the other hand, pulsatile behavior of a signal associated with the cerebellum does not facilitate measurement of oxygenation in the brain.

Clinical systems provide a measure of both pulse oximetry and regional oximetry using a variety of optical sensors that interface with a processor. A clinical system can be powered by metered line service and, in some instances, using multiple processors.

In field settings, however, the power demands to provide both pulse oximetry and regional oximetry have resulted in devices that are rather large and suffer poor battery life.

Overview

The present inventors have recognized, among other things, that a problem to be solved can include providing both pulse oximetry and regional oximetry in a compact package that enable simplified physiological measurements. The present subject matter can help provide a solution to this problem, such as by using multiple emitters and detectors affixed to various surfaces and activated in a coordinated manner to provide low noise measurement of both pulse oximetry and regional oximetry.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 1 illustrates a digit probe, according to one example.

FIG. 2 illustrates a digit probe, according to one example.

FIG. 3 illustrates a block diagram of a device, according to one example.

FIG. 4 illustrates a digit probe, according to one example.

FIG. 5 illustrates a digit probe, according to one example.

FIGS. 6 and 7 illustrate a digit probe in a first and second configuration, according to one example.

FIG. 8 illustrates a patient fitted with two devices, according to one example.

FIG. 9 illustrates a flow chart, according to one example.

FIG. 10 illustrates a device, according to one example.

DETAILED DESCRIPTION

FIG. 1 illustrates device 100A, sometimes referred to as a digit probe, according to one example. Device 100A includes upper jaw 16A coupled to lower jaw 12A by a joint. The joint in this example includes an articulating hinge having a dynamic pivot axis. A curved feature on the sides of upper jaw 16A and a corresponding feature on the lower jaw 12A is adapted to mesh when the jaws are brought together. A spring or elastic element is fitted to the jaws and urges the jaws to a closed position.

Interior surface 18A is disposed on an interior portion of upper jaw 16A and interior surface 14A is disposed on an interior portion of lower jaw 12A. Interior surface 18A and interior surface 14A are configured to receive a digit, such as a finger or toe, in the example illustrated. Other configurations are also contemplated, including an embodiment suited for affixation at an ear lobe.

Optical elements 20A and 20B are fitted to interior surface 18A and 14A, respectively. Optical elements 20A and 20B can include any combination of an emitter and a detector. An emitter can include a fiber optic element or a light emitting diode (LED) suited for emission at a particular wavelength or selected wavelengths. An optical detector can include a photodetector having sensitivity at a particular wavelength and can include an electrical terminal for providing an electrical signal corresponding to detected light energy.

In this example, optical elements 20A and 20B include an emitter and a detector and are configured for determining pulse oximetry.

FIG. 2 illustrates a view of lower jaw 12A of device 100A. Lower jaw 12A is shown in a closed configuration relative to upper jaw 16A. Lower jaw 12A is configured with a plurality of optical elements disposed near corners of the generally rectangular shape of contact surface 10A of lower jaw 12A. The plurality of optical elements includes optical element 20C, optical element 20D, optical element 20E, and optical element 20F.

In this example, optical element 20C, optical element 20D, optical element 20E, and optical element 20F includes at least one emitter and at least one detector and are configured for determining regional oximetry.

Port 42 is an electrical connection accessible from an external surface of device 100A. Port 42 can enable coupling of device 100A with an auxiliary sensor or other device. Port 42 can be referred to as a sensor port. In the example shown, port 42 is affixed to lower jaw 12A, however, in other examples, port 42 is affixed to upper jaw 16A.

Port 42 can carry an analog signal, digital data, or power, and in one example port 42 can be used to configure device 100A for measuring regional oximetry ($rSO_2$), pulse oximetry ($SpO_2$), or any other compatible external sensor by plugging into the appropriate port.

An auxiliary sensor can include an external $rSO_2$ sensor or an $SpO_2$ probe suited for use with a particular tissue site (such as an ear probe or a forehead probe). In various examples, a processor internal to device 100A (such as processor 84 discussed elsewhere in conjunction with FIG. 3) or a manually operated switch coupled to device 100A can be used to configure device 100A to a configuration suitable for a particular selected physiological parameter measurement. Alternately, in an example, the device can also have a separate analog front end for each optical element. The figure illustrates a single port (here referenced as port 42) and in some examples, more than one port is provide on an external surface.

Figure 3:
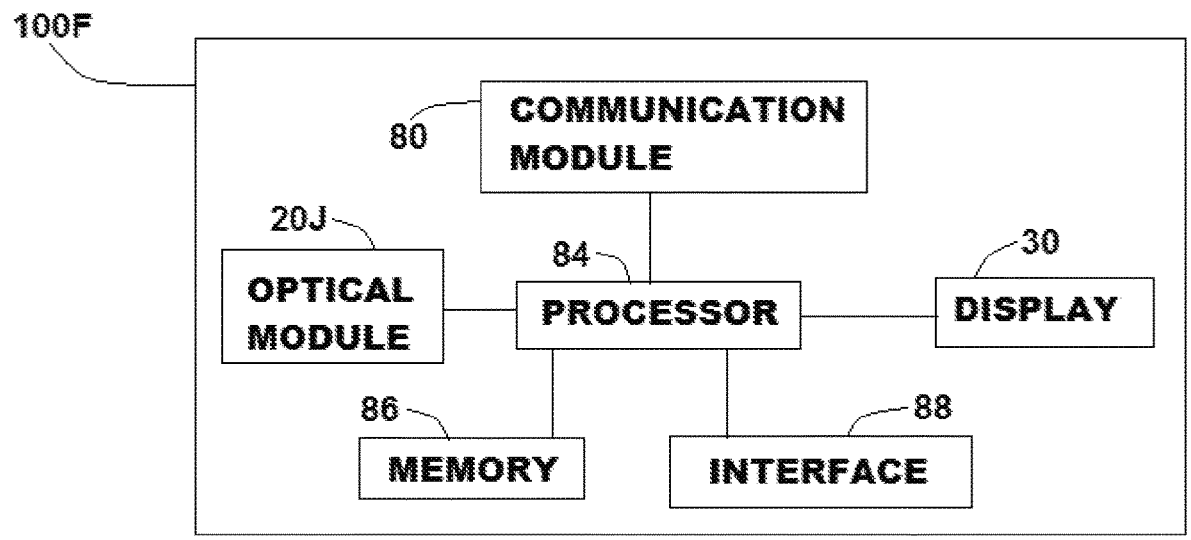

FIG. 3 illustrates a block diagram of device 100F, according to one example. Device 100F includes optical module 20J, processor 84, memory 86, interface 88, communication module 80, and display 30. Optical module 20J, processor 84, memory 86, interface 88, communication module 80, and display 30 can each be located in upper jaw 16A, for example, located in lower jaw 12A, or some portion can be located in upper jaw 16A and some portion can be located in lower jaw 12A.

Optical module 20J can include any number of separate optical elements, some examples of which are represented by optical elements 20A-20F in other portions of this document. Optical module 20J can be configured for transmission through tissue or configured for reflectance measurement in which light reflected from the tissue site provides a measurement signal associated with a physiological parameter. The separate optical elements of optical module 20J can include any combination of internal or external elements. For example, optical module 20J can include an emitter and a detector affixed directly to a housing of device 100F or optical module 20J can include an auxiliary sensor having an emitter and a detector coupled by an electrical cord or an optical fiber.

Processor 84 is coupled to optical module 20J. Processor 84 is configured to provide a drive current to a portion of optical module 20J and configured to receive an electrical signal corresponding to a detected light emission. Processor 84, in various configurations, includes a driver circuit, a filter, an analog-to-digital converter, a digital-to-analog converter, an amplifier, a microprocessor, and other elements.

Processor 84 is coupled to memory 86. Memory 86 provides storage for data corresponding to a measured physiological parameter, calibration information, authentication information, patient information, communication parameters, and other data, and provides storage for instructions for execution by processor 84.

Interface 88 is coupled to processor 84 and can include a graphical user interface by which a user can interact with device 100F. For example, interface 88 can include a touch-sensitive screen, any number of switches or controls, and can include a display or an indicator light to show device activity or readiness.

Communication module 80 can include wired or wireless telemetry module. For example, communication module 80 can include a radio frequency (RF) receiver, an RF transmitter, or an RF transceiver. In various examples module 80 can include a Bluetooth or low power radio communication module. In various examples, communication module 80 can include a wired port configured to electrically connect with a cable or connector.

Display 30 can include an indicator light, visible display of characters, an LED emitter or other indicator to show a physiological measurement, the condition of the device, the state of the device, device activity, calibration information, device settings, patient identification information, communication channel information, paired devices in a communication network, synchronization status information, or other information.

Figure 1:
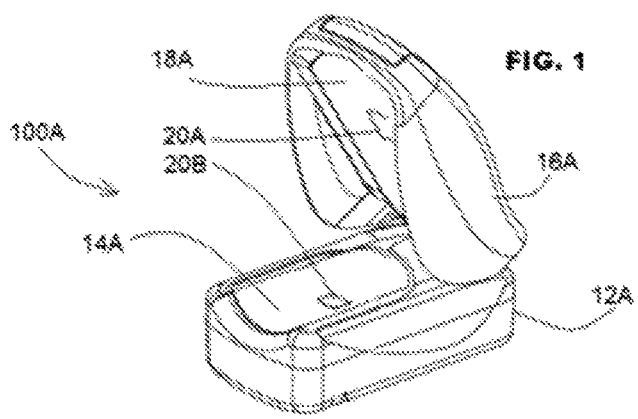
Figure 2:
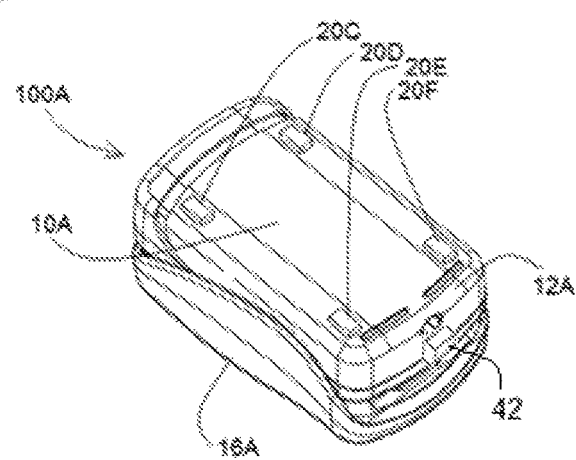
Figure 4:
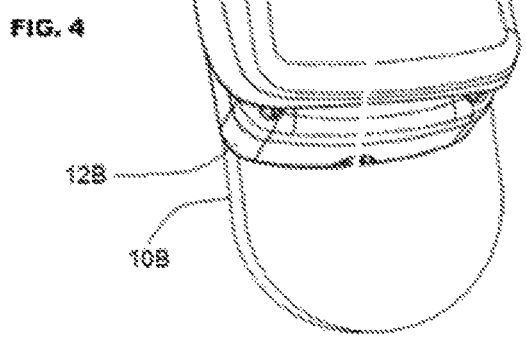

FIG. 4 illustrates device 100B having display 30 coupled to upper jaw 16B. In this example, lower jaw 12B is coupled to contact surface 10B. Contact surface 10B includes elements that provide a region of contact on the tissue surface that has sufficient length to allow measurement of regional oximetry. In the example shown, contact surface 10B provides spacing that allows measurement of light energy along multiple pathways through the tissue. Contact surface 10B can be electrically or mechanically coupled to a corresponding feature of lower jaw 12B. In the example shown, display 30 illustrates two lines of numerical data and a heart icon that can be modulated to show device activity and measurement.

Figure 5:
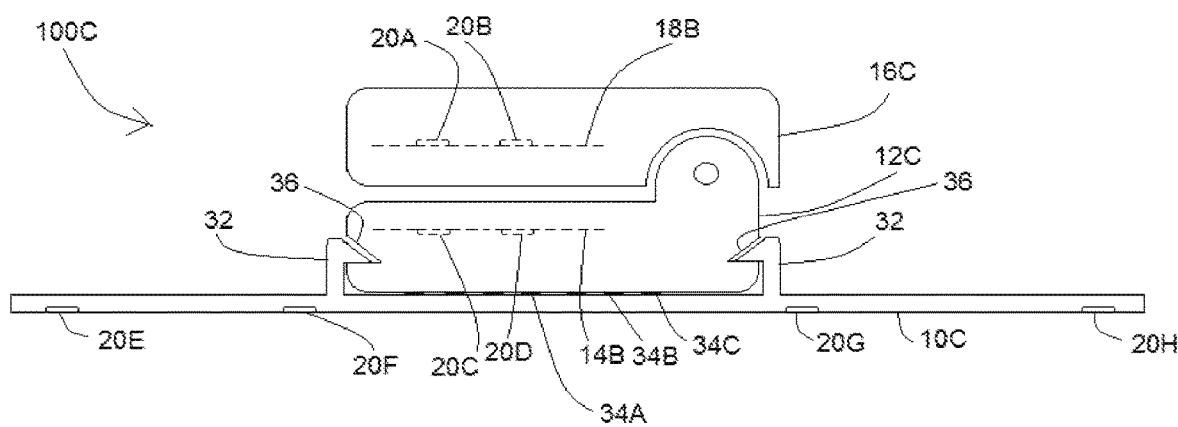

FIG. 5 illustrates a view of device 100C, according to one example. Device 100C includes an upper jaw 16C jointly coupled to lower jaw 12C. Upper jaw 16C includes interior surface 18B, here shown in dashed lines. In addition, interior surface 18B is fitted with optical elements 20A and 20B. Lower jaw 12C includes interior surface 14B, here shown in dashed lines. In addition, interior surface 14B is fitted with optical elements 20C and 20D.

In the example shown, lower jaw 12C includes notches 36 on opposing ends. Notches 36 are configured to engage with catch feature 32 disposed on a side of contact surface 10C. Contact surface 10C and lower jaw 12C are electrically coupled by a plurality of electrical contacts 34A, 34B, and 34C at a mating surface. Contact surface 10C includes a plurality of optical elements 20E, 20F, 20G, and 20H, some of which can include at least one emitter and at least one detector. In one example, electrical contacts 34A, 34B, 34C provides drive current to emitters and measured signal conduction from detectors of the plurality of optical elements.

In one example, an optical element is coupled by a translucent conduit. For example, the translucent conduit can include a resin, an epoxy, a light pipe, or a fiber optic element. For example, a translucent conduit can be configured to carry emitted light between a tissue site and an optical element in either a unidirectional manner or a bidirectional manner.

Catch feature 32 includes an elastically mounted pawl that engages with notch 36 to retain contact surface 10C in a fixed position relative to lower jaw 12C. In one example, an electrical connector on a cord can be used to provide an electrical connection between contact surface 10C and lower jaw 12*c*.

FIGS. 6 and 7 illustrate a digit probe in a first and second configuration, according to one example. Device 100D represents a configuration suited for pulse oximetry in which upper jaw 16C and lower jaw 12D are in closed configuration having optical elements 20A, 20B, 20C, and 20D disposed on opposing regions of digit 60. Interior surface 18C and interior surface 14C are in facing alignment. Upper jaw 16C and lower jaw 12D are jointly coupled by link 38.

Device 100E represents a configuration suited for regional oximetry in which upper jaw 16C and lower jaw 12D are in an open configuration, as shown by the inverted reference character 'B' on lower jaw 12D. In the open configuration, optical elements 20A, 20B, 20C, and 20D are disposed along a common contact surface and device 100E is configured for regional oximetry. In various examples, one set of the optical elements are operated to provide a measure of regional oximetry and a second set (different from the first set) is operated to provide a measure of pulse oximetry. In the example illustrated, tissue 62 is shown in contact with the optical elements 20A, 20B, 20C, and 20D. Link 38 provides freedom of movement to allow upper jaw 16C and lower jaw 12D to align as shown.

Consider an example in which optical elements 20A and 20C are emitters and optical elements 20B and 20D are detectors in a configuration for reflectance measurement. In this configuration, light energy from optical element 20A is emitted into tissue 62 and detected by detector of optical element 20B, along light pathway 52A, as well as detector of optical element 20D, along light pathway 54A. In a similar manner, light energy from optical element 20C is emitted into tissue 62 and detected by detector of optical element 20D, along light pathway 52B, as well as detector of optical element 20B, along light pathway 54B. The multiple pathways allows calculation of regional oximetry using a sum and difference method that reduces the influence of noise and surface artifacts. For a transmittance mode of operation, a different set of optical elements can be activated.

Figure 8:
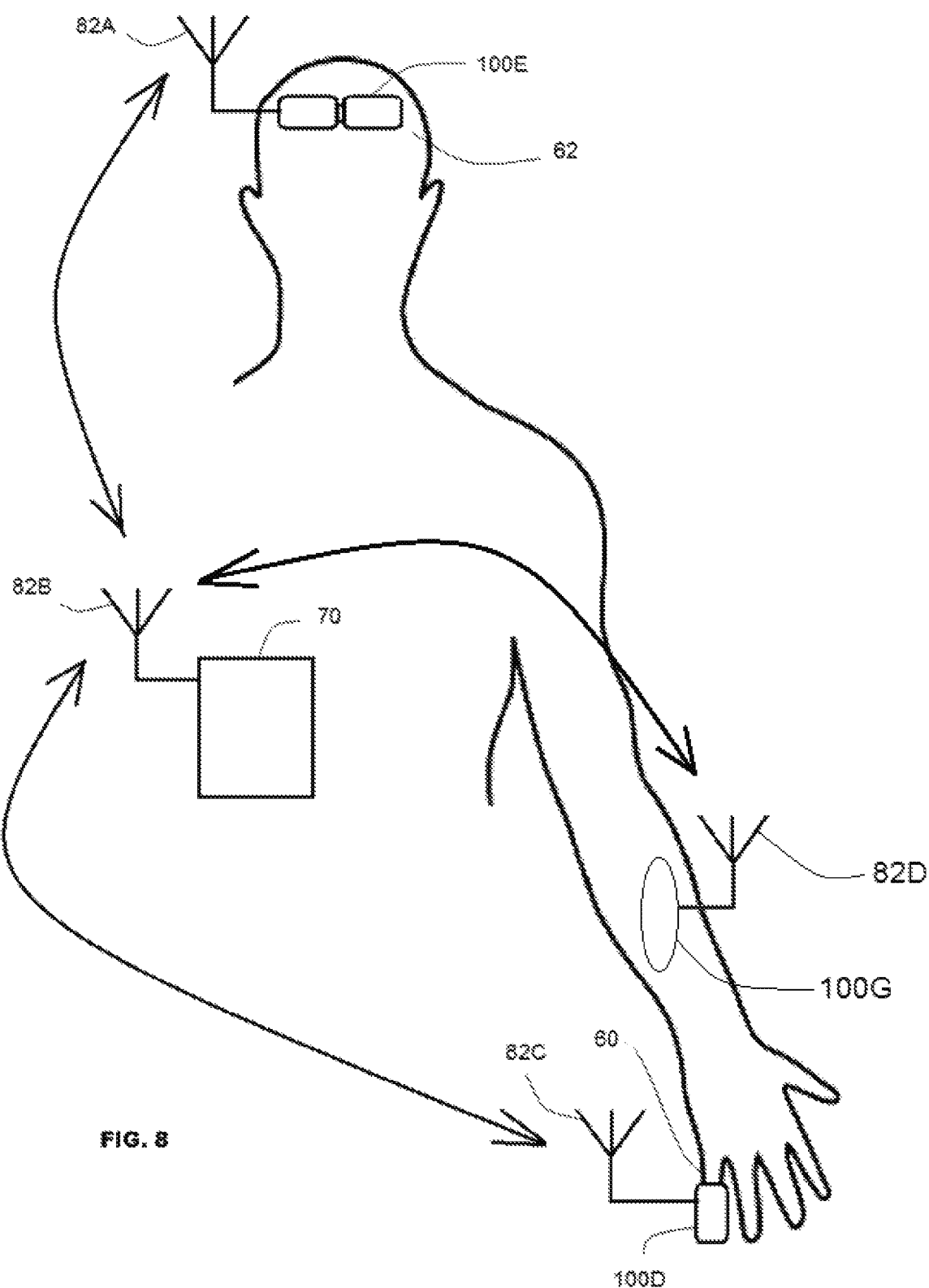

FIG. 8 illustrates a patient fitted with device 100E, device 100D, and device 100G. In this example, device 100E provides a measure of regional oximetry at tissue site 62. Here, tissue site 62 can represent cerebral oximetry. In addition, device 100D is affixed to finger 62 in the manner of pulse oximetry. Device 100G is affixed to a forearm location and can be configured to provide regional oximetry measurements suitable for monitoring for shock. In this example, device 100D and device 100E are structurally matched but in one instance, the jaws are in an open configuration and in the other instance, the jaws are in the closed configuration.

Device 100E is fitted with RF antenna 82A, device 100D is fitted with RF antenna 82C, and device 100G is fitted with RF antenna 82D. Antennas 82A, 82C, and 82D can be internal to the device and represented as a component of communication module 80 described elsewhere in this document. In one example, antennas 82A, 82C, and 82D are external to the device. Remote device 70 is fitted with antenna 82B. In various examples, remote device 70 is body worn or is at a distance from the user. Remote device 70, in one example provides synchronization to allow device 100E, device 100D, and device 100G to operate without interfering with each other. For example, optical emissions from an emitter of device 100D can provide additional input that can alter the measured signal provided by device 100D or device 100G. In one example, synchronization includes controlling emissions in a manner that includes dead time between signal readings to avoid sensor crosstalk.

Figure 9:
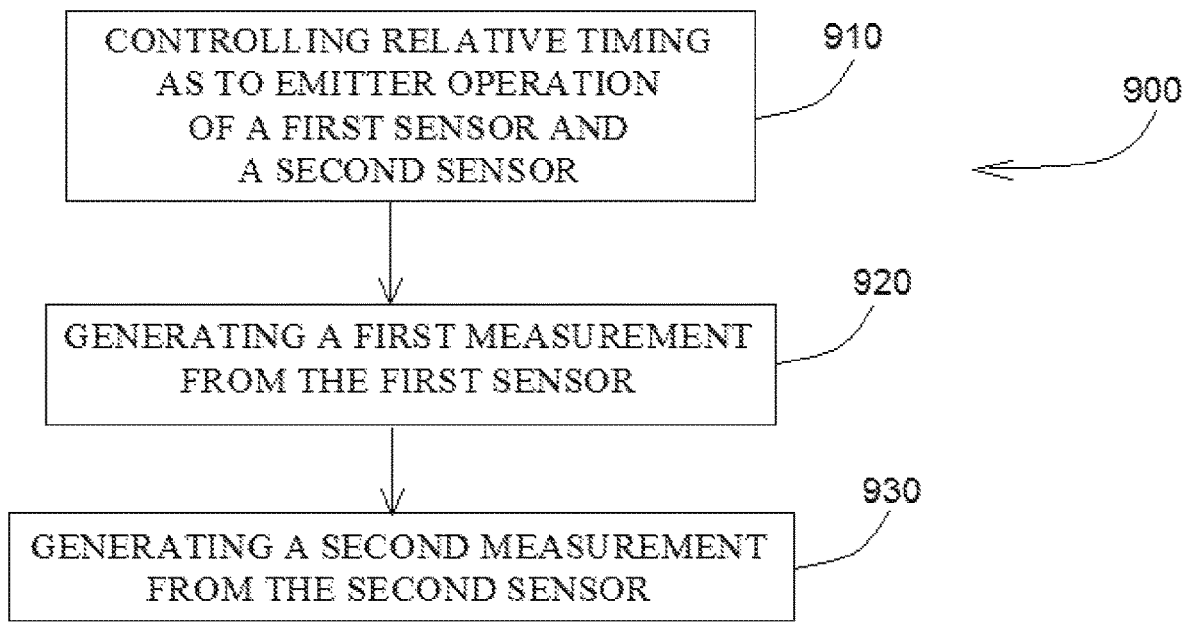

FIG. 9 illustrates a flow chart of method 900, according to one example. At 910, the method includes controlling relative timing as to emitter operation of a first sensor and a second sensor. At 920, the method includes generating a first measurement from the first sensor, and at 930, the method includes generating a second measurement from the second sensor. In this manner, the devices can be operated without interference. For example, synchronization can be provide by a remote device, such as device 70. In one example, synchronization is provided by one device operating as a master and establishing all other devices in the system as slaves.

In one example, a handshake protocol can determine classification of devices in a system. In one example, a master clock provides a timing signal to other elements to ensure precision LED timing to allow for signal processing and for noise and artifact reduction.

Figure 10:
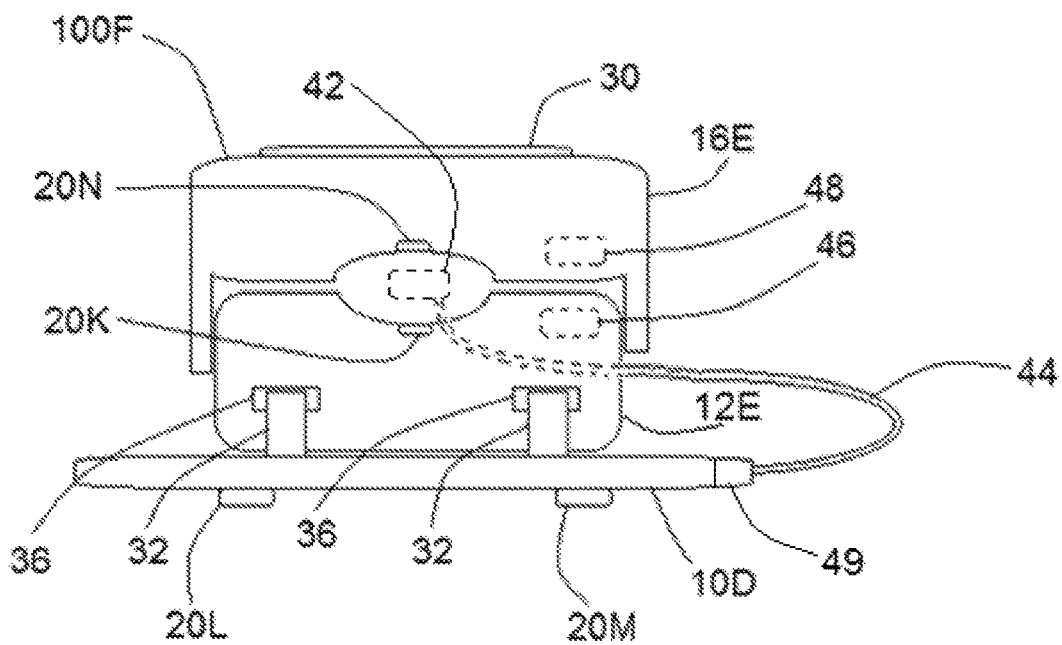

FIG. 10 illustrates device 100F, according to one example. Device 100F includes upper jaw 16E (sometimes referred to as display-side jaw) coupled to lower jaw 12E (sometimes referred to as non-display-side jaw). Upper jaw 16E is coupled to display 30 and includes optical element 20N. Port 48 is accessible on a back side of upper jaw 16E and provides an electrical connection to enable certain device functions.

Lower jaw 12E includes optical element 20K and is affixed to contact surface 10D by catches 32 and notches 36. Port 46 is accessible on a back side of lower jaw 12E and provides an electrical connection to enable certain device functions.

Contact surface 10D is physically separable from lower jaw 12E and includes optical elements, some of which are denoted here as optical element 20L and optical element 20M. Contact surface 10D can be electrically connected to a particular port of device 100F by link 44.

In one example, certain electronic components such, such as those shown in FIG. 3, are housed in lower jaw 12E.

Port 42, port 46, and port 48 can each be configured for various applications. For example, contact surface 10D can be coupled, via connector 49 and link 44, to port 42 (as shown in FIG. 10), or to port 46, or to port 48. These configurations enable various measurements, such as $rSO_2$ measurement or $SpO_2$ measurement. As another example, an electrical conductor coupled to port 42 can be connected to connector 48 on the upper jaw 16E. This configuration is suitable for pulse oximetry measurement. In one example, an electrical conductor coupled to port 42 can be connected to an external sensor and suited for an application based on the external sensor. In another example, port 42 can be left open in which case, no measurement is provided.

Any one or more of port 42, port 46, and port 48 can each be configured for connecting to an external device. For example, an external device can include a site-specific sensor such as a forehead sensor or an ear sensor. In addition, an external device can include a long-cabled wired connector, such as an $rSO_2$ sensor. Furthermore, any such port can be configured to communicate with, and electrically connect with, an external sensor, some examples of which can include: a pulse oximetry sensor, a disposable sensor, a reusable sensor, a flexible substrate sensor, a wrist-worn sensor, a capnography sensor, a regional oximetry sensor, a neonatal sensor, a pediatric sensor, and a veterinary sensor. In one example, a port of the present subject matter is configured to connect with a patient interface carrier ($rSO_2$ without cable) and a display (such as display 30) is configured to automatically display relevant parameters. In one example, the display content can be configured for a particular visual configuration of data and information based on a control signal provided by the processor.

Various Notes & Examples

A number of other configurations are also contemplated. For example, in embodiment includes a sensor device having a first leaf and a second leaf. Both the first leaf and the second leaf have an interior surface and an exterior surface. At least one surface is configured with an optical element. A joint couples the first leaf and the second leaf.

A sensor, according to one example, includes a first emitter and a second emitter wherein each emitter is configured to emit light directed to a tissue site. A first detector is configured to provide an electrical signal corresponding to light from the tissue site. The light from the tissue site corresponds to the emitted light from at least one of the first emitter and the second emitter. A processor is coupled to the first emitter, the second emitter, and the detector and wherein the processor is configured to execute instructions to determine regional oximetry corresponding to the tissue site and to determine pulse oximetry corresponding to arterial oxygenation of blood at the tissue site. A communication module is coupled to the processor. The communication module is configured to telemeter data between the processor and a remote device.

In one example, at least one of the first emitter, the second emitter, and the detector are disposed on an interior surface of a digit probe.

In one example, at least one of the first emitter, the second emitter, and the detector are disposed on an exterior surface of a digit probe.

In one example, at least one of the first emitter, the second emitter, and the detector are disposed on an interior surface of a digit probe.

The plurality of optical elements can include two emitters and one detector. This can include two light emitting diodes (LEDs) and one photodetector. The emitter, and the photodetector are selected to have a particular amplitude at a specified wavelength.

A first device can be in wireless communication with a second device or in wireless communication with a remote device. In one example, communication entails a wired connection. Wireless telemetry can allow for synchronization and for data processing and data compilation. In an example device having a wireless communication module, a battery provides a power supply.

In addition to measuring pulse oximetry and regional oximetry, other physiological parameters can also be measured using various examples of the present subject matter. For example, a device can be configured to measure carboxyhemoglobin, methemoglobin, total hemoglobin, pulse wave velocity, heart rate variability, pulse rate, respiration rate, and other parameters.

An optical element can include a surface mounted component. In one example, the optical elements are configured for transmittance measurement of oxygenation. In one example, reflectance measurement is performed.

In an example of an implementation having multiple devices on a single patient, the resulting data can be compiled at a single device, at multiple devices, or at a remote monitor in communication with the multiple devices. In one example, data is conveyed from one device to another device in a daisy-chain manner. Synchronization and communication enables selection of a measurement and communication time slot in a manner that reduces or eliminates interference from other nearby devices.

Handshaking and pairing routines can be implemented to ensure that data associated with one user does not interfere or contaminate data associated with a different user.

In one example, an application specific integrated circuit (ASIC) provides an interface between the optical module and the processor and allows for low power operation and functionality.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A device comprising:
    a digit probe having a housing with an interior surface and having an opposing exterior surface, wherein the interior surface is configured to engage a digit and the exterior surface is configured to engage a tissue site;
    a plurality of optical elements coupled to at least one of the interior surface and the exterior surface, the plurality of optical elements including at least one emitter and including at least one detector;
    a processor coupled to the plurality of optical elements, the processor configured to generate a first physiological measurement corresponding to the digit and configured to generate a second physiological measurement corresponding to the tissue site; and
    a communication module coupled to the processor, wherein the communication module is configured to communicate the first physiological measurement and the second with a remote device.

2. The device of claim 1 wherein the housing includes a first jaw jointedly coupled to a second jaw.

3. The device of claim 2 wherein the interior surface is disposed on a portion of the first jaw proximate to the second jaw.

4. The device of claim 2 wherein the exterior surface is disposed on a portion of the first jaw distal to the second jaw.

5. The device of claim 1 wherein the plurality of optical elements includes at least a first detector and a second detector and wherein the processor is configured to synchronize relative timing as to a drive signal provided to the first detector and to the second detector.

6. The device of claim 1 wherein the plurality of optical elements includes at least a first emitter and a second emitter, and wherein the processor is configured to synchronize relative timing as to a drive signal provided to the first emitter and to the second emitter.

7. The device of claim 1 further including a display coupled to the digit probe.

8. The device of claim 7 wherein the display is configured to provide a visible indication of at least one of arterial oxygenation and regional oxygenation.

9. The device of claim 1 wherein the first physiological measurement includes a measurement of pulse oximetry.

10. The device of claim 1 wherein the second physiological measurement includes a measurement of regional oximetry.

11. The device of claim 1 wherein the communication module includes at least one of a wireless transmitter, a wireless receiver, and a wireless transceiver.

* * * * *